(12) United States Patent
Forell et al.

(10) Patent No.: US 10,568,730 B2
(45) Date of Patent: Feb. 25, 2020

(54) URETHRAL STENT AND BLADDER CONTROL ASSEMBLY COMPRISING SUCH A URETHRAL STENT

(71) Applicant: DENTSPLY IH AB, Mölndal (SE)

(72) Inventors: Johanna Forell, Mölndal (SE); Elin Johansson, Göteborg (SE); Jenny Mottare, Göteborg (SE); Jan Utas, Kungsbacka (SE)

(73) Assignee: DENTSPLY IH AB, Mölndal (SE)

( * ) Notice: Subject to any disclaimer, the term of this patent is extended or adjusted under 35 U.S.C. 154(b) by 0 days.

(21) Appl. No.: 16/435,847

(22) Filed: Jun. 10, 2019

(65) Prior Publication Data

US 2019/0374329 A1 Dec. 12, 2019

(30) Foreign Application Priority Data

Jun. 11, 2018 (EP) .................................... 18176987

(51) Int. Cl.
*A61F 2/04* (2013.01)
*A61F 2/88* (2006.01)

(52) U.S. Cl.
CPC .......... *A61F 2/04* (2013.01); *A61F 2002/047* (2013.01); *A61F 2210/009* (2013.01); *A61F 2220/0008* (2013.01); *A61F 2230/005* (2013.01)

(58) Field of Classification Search
CPC .... A61F 2/04; A61F 2/42; A61F 2/042; A61F 2/88
USPC ............................................ 623/23.64–23.66
See application file for complete search history.

(56) References Cited

U.S. PATENT DOCUMENTS

| 5,366,506 A | 11/1994 | Davis |
| 5,782,916 A * | 7/1998 | Pintauro ............... A61F 2/0022 600/30 |
| 5,996,585 A | 12/1999 | Migachyov |
| 6,707,360 B2 | 3/2004 | Underwood et al. |
| 7,012,495 B2 | 3/2006 | Underwood et al. |
| 9,622,848 B2 * | 4/2017 | Lund ........................ A61F 2/04 |
| 2004/0068252 A1 | 4/2004 | Whitmore et al. |

(Continued)

FOREIGN PATENT DOCUMENTS

| DE | 2537506 | 3/1977 |
| WO | 2012059906 | 5/2012 |
| WO | 2013144770 | 10/2013 |

OTHER PUBLICATIONS

Search Report for European Patent Application No. 18176987.8, dated Dec. 21, 2018 (7 pages).

*Primary Examiner* — Suzette J Gherbi
(74) *Attorney, Agent, or Firm* — Perkins Coie LLP

(57) ABSTRACT

A urethral stent for arrangement in the urethra of a patient is disclosed. The ethereal stent includes a tubular body having first and second openings, retention elements connected to the tubular body at the first opening and to the tubular body at a distance from the first retention element, and a valve. The valve includes a valve seat formed by the first opening and a valve element that is pivotably connected to the tubular body and/or the valve seat. The valve is pivotable between a closed position and an open position to close and open the lumen, respectively. The valve is at least partly made of a ferromagnetic material and has an area which exceeds the area of the first opening. A bladder control assembly comprising the urethral stent is also disclosed.

20 Claims, 3 Drawing Sheets

(56) References Cited

U.S. PATENT DOCUMENTS

| | | | |
|---|---|---|---|
| 2005/0240280 A1* | 10/2005 | Aliski | ................. A61F 2/04 623/23.68 |
| 2012/0238803 A1 | 9/2012 | Lund | |
| 2015/0087896 A1 | 3/2015 | Wei et al. | |
| 2019/0030303 A1* | 1/2019 | Holman | ............. A61M 25/04 |

* cited by examiner

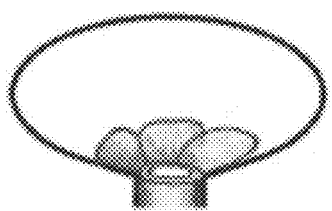 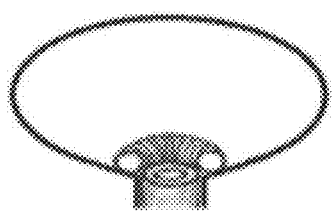 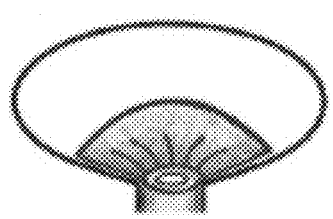
Fig. 7a          Fig. 7b          Fig. 7c
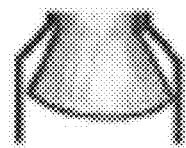 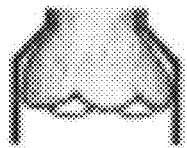 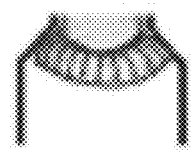
Fig. 8a          Fig. 8b          Fig. 8c

URETHRAL STENT AND BLADDER CONTROL ASSEMBLY COMPRISING SUCH A URETHRAL STENT

CROSS REFERENCE TO RELATED APPLICATIONS

This patent document claims the benefits and priority of European Patent Convention Application No. 18176987.8, filed on Jun. 11, 2018, which is incorporated herein by reference in its entirety.

FIELD OF THE INVENTION

The disclosed embodiments relate to a urethral stent for insertion into the urethra of a patient, and including an externally operable valve. It further relates to a bladder control assembly including such a urethral stent.

BACKGROUND

Urinary dysfunctions in the lower urinary tract can occur due to detrusor dysfunctions, various sensory bladder disorders, and sphincter dysfunctions. These dysfunctions, in turn, can be divided into storage, voiding, and postmicturition symptoms. The dysfunctions are generally due to overactive or underactive detrusor and/or sphincter.

Dysfunction in the detrusor and sphincter muscles can have multiple causes and a number of different symptoms. Common for all urinary disorders is that the storage phase or the voiding phase of the bladder is affected. When a patient has issues with the storage phase it may appear as urinary incontinence while problems with the voiding phase may lead to urinary retention. Thus, incontinence causes leakage in the storage phase, while retention causes inability to void voluntarily and/or residual urine after voiding. These are the most common urinary disorders.

Urinary retention (UR) is a condition where the urinary bladder is unable to void urine completely. This can be caused by blockages of the urethra, nerve problems, medications, weakened bladder muscles, or as a side effect to treatment of urinary incontinence. Issues that may cause UR include prostate enlargement, vaginal childbirth, brain or spinal cord infections or injuries, diabetes, stroke, MS, pelvic injury or trauma, or heavy metal poisoning.

Urinary incontinence (UI) is the involuntary leakage of urine from the urinary bladder. It is a large and ever growing problem, and it is e.g. expected that most women are affected at some point in their life. Urinary incontinence is generally caused by an underactive sphincter, where it cannot contract properly since the sphincter cannot keep tight and leakage may occur. Reasons for having an underactive sphincter could be complex vaginal deliveries, gynecological surgeries, radiation damages, unsuccessful urological procedures, etc. An overactive sphincter is contracted most of the time which may lead to voiding symptoms, such as urinary retention. Urinary incontinence can also occur due to having an overactive bladder, which is when nerves send signals to the bladder to micturate at the wrong time.

Known treatments or managements for urinary incontinence comprises incontinence products, such as incontinence pads, catheterization products, and surgery.

Many attempts have been made to provide stents and other insertable or implantable products that would be useful for bladder control, to overcome the problems related to UI or UR.

For example, U.S. Pat. No. 5,782,916 discloses a prosthetic device having first anchor means to be arranged in the bladder, and second anchor means to remain in the urethra, and a tubular element with a duck-bill valve. However, this device is intended to drain urine by voluntarily increasing the pressure in the bladder. However, in practice, this would inevitably lead to leakage, when coughing, laughing, lifting heavy loads, exercising, etc.

Further, DE 2537506 is an old example of an implantable prosthetic device, having a magnetic valve, which is operated by an external magnet. However, this device needs to be fixed to the urethra by surgery, making the processes of inserting, removing and replacing the device both costly and potentially hazardous. Further, the valve is difficult to control properly, and would require a very large magnet to work, which is highly unpractical for practicing in daily life.

Still further, U.S. Pat. No. 5,366,506 discloses a urethral magnet valve for placement in the urethra, and which is controllable by an external magnet. However, this product would also be difficult to control properly, and would require the use of very large magnets.

U.S. Pat. No. 5,996,585, finally, discloses a device for housing a valve, and with retention elements to maintain the device in place. However, since the device extends out from the urethra at one end, thereby significantly increasing the risk of urinary tract infections and the like.

A general problem related to such known devices is also that the space available for inserting the device into the urethra, and for housing the valve within the urethra, is very limited. The female urethra is e.g. typically 6-8 mm in diameter, in expanded state, during voiding, which means that the device need to be compressible to such dimensions in order to be able to insert it without surgical procedures, and without causing pain and damage to the patient. Further, arranging a structure also comprising a valve device in the urethra by necessity severely limits the available lumen area for the urine to be drained out. Thus, most of the prior art devices would have insufficient drainage capacity, leading to insufficient drainage, and also a very tedious draining process.

A further general problem with the known devices is that in case of malfunction, it is difficult or even impossible to drain urine out of the bladder. The only solution would often be to remove the device, e.g. with a surgical procedure. This is an expensive and cumbersome procedure. Further, if this is not done relatively quickly, the overfilling of the bladder will cause pain for the patient, and may also be dangerous and life-threatening. For example, there is a risk that urine will flow back into the ureters and damage the kidneys.

There is therefore a need for a new and improved urethral device which addresses these issues, and in particular a urethral device which can be controlled efficiently by the user, thereby providing drainage only at will and alleviating the need of leakage at other times, which is small enough to be inserted in a fast, reliable and painless way, which provides adequate draining flow rate, which can be maintained inserted/implanted for a long period of time, with minimal risk of urinary tract infections and the like, which can be easily emergency drained in case of malfunction, and/or which can be produced and used cost-effectively. In particular, there is a need for such a urethral stent which can be used for women suffering from urinary incontinence due to an underactive sphincter.

SUMMARY OF THE INVENTION

It is therefore an object of the disclosed embodiments to provide a urethral stent and a bladder control assembly which at least alleviates the above-discussed problems.

This object is obtained by a urethral stent and a bladder control assembly in accordance with the appended claims.

According to a first aspect of the disclosed embodiments there is provided a urethral stent for arrangement in the urethra of a patient, comprising:

a tubular body having a first end with a first opening and a second end with a second opening, and a wall defining a lumen extending therethrough between the first and second openings;

at least one first retention element connected to the tubular body at, or in the vicinity of, the first end;

at least one second retention element, connected to the tubular body at a distance from the first end and the first retention element;

a valve arranged at the first end, the valve comprising a valve seat formed by the first opening and a valve element being pivotably connected to the tubular body and/or the valve seat by a hinge connected to the tubular body and/or to the valve seat at one side of the first opening, whereby the valve element is pivotable between a closed position, in which the valve element is in engagement with the valve seat at the first opening, thereby closing the lumen, and an open position in which the valve element is pivoted away from the valve seat, thereby opening the lumen, wherein the valve element is at least partly made of a ferromagnetic material and has an area which exceeds the area of the first opening, and preferably also exceeding the area of the lumen; and at least one pivot restriction element arranged in the vicinity of the first opening and in the vicinity of the hinge, and protruding away from tubular body.

This urethral stent has been found to be very efficient. The provision of a pivotable valve element with ferromagnetic material makes the valve controllable from outside the patient, by operation of an external magnet or the like. This makes draining of the bladder very easy and convenient, since the patient just needs to position an external magnet at an appropriate part of the body to open the valve. Further, since the valve is arranged on top of the tubular body, the valve element can be made much larger than if it had been arranged inside the tubular body. This is very beneficial for many reasons. First of all, a larger valve element provides a greater attraction to the external magnet, making it possible to use a smaller external magnet. Large external magnets are heavy and impractical to carry around, which limits the life quality of the user. Further, large magnets would cause when carried around, such as demagnetizing credit cards, etc. Secondly, the large pivotable valve element makes it possible to have a relatively large drainage lumen, making draining more efficient. Thirdly, since the valve is arranged on top of the tubular body, the total cross-sectional dimensions when the stent is compressed for insertion and removal are very limited, despite the relatively large dimensions of the valve element in itself, thereby making insertion and removal easier, quicker and painless. The arrangement of the valve element at the top of the tubular body also ensures that the valve is fully closed at all times, unless it is deliberately opened by use of an external magnet. The valve element will be pressed down onto the valve seat both by gravity and by the internal pressure of urine within the bladder, thereby maintaining a leakage free closure at all times, even if the bladder pressure suddenly increases, such as when coughing, laughing, etc. Still further, the provision of a valve element arranged at the top of the tubular body, and which pivots upwards to be opened, also makes it easily accessible for emergency opening, should that be necessary. The patient, or anyone else, can easily emergency open the valve by e.g. inserting a small catheter, stent or the like into the urethra. The catheter/stent will then proceed into the tubular body, and push the valve element to an open position.

Since the urethral stent is fully accommodated by the urethra and bladder in the use position, without any parts extending out from the urethra orifice, the risk of infections are minimized. Hereby, the stent can also remain inserted for a very long time, such as for weeks, a month, several months, or even longer.

The urethral stent is also easy and cost-effective to produce, since it has relatively few parts, and operates in a purely mechanical manner, and is also easy and cost-effective to use, since it is easy to insert and remove, efficiently reduces health problems and improves life quality of the patient. It is also easy and convenient to introduce and remove, without any need for surgery.

The urethral stent is particularly suited for women suffering from urinary incontinence due to an underactive sphincter. However, it may also be used for treatment of other female urinary dysfunctions, such as urinary retention. Still further, it can also be used for male patients.

The provision of the first and second retention elements ensures that the stent will remain in place in its position, extending from the upper part of the urethra and into the bladder, at all times, and makes insertion and removal of the stent simple and quick.

The new stent provides safe, comfortable and discrete treatment for patients having urinary dysfunctions, such as women with severe urinary incontinence, allowing them to have much improved control of their urination. The stent is preferably inserted and removed by medical professionals, such as at primary care, but can when in place be operated by the patient himself/herself.

The pivot restriction element restricts the pivoting of the valve element when opened. The pivoting could e.g. be restricted to be below 90 degrees, and preferably to a maximal opening angle in the range of 30-80 degrees, such as 40-70 degrees, such as 50-60 degrees. By restricting the opening angle, it is ensured that the valve element will by itself, automatically, return to a closed position when the attraction force from the external magnet is removed. The pivot restriction element(s) could e.g. comprise at least one finger extending essentially in the length direction of the tubular body. In a preferred embodiment, one such finger is provided on each side of the hinge, thereby providing an equal support on both sides for the valve element when opened.

To further promote return of the valve element when the magnetic attraction ceases, the hinge may further have a bias, urging the hinge to return to the closed valve position when there is no external magnetic attraction present.

The valve element may comprise a disc of ferromagnetic material. The disc is preferably a solid, flat disc, and may have a circular or close to circular shape. Preferably, the shape of the disk resembles the shape of the first opening.

The hinge may be of an elastic plastic material, and preferably a polymer material, such as silicone rubber, and may be made integral with the tubular body. For example, the hinge may be formed monolithically with the tubular body. However, it may also be made separately, and connected to the tubular body by welding, adhesion, gluing, or the like. The hinge may be attached to the ferromagnetic material, e.g. in the form of a disc, by adhesive, gluing overmolding, or the like.

In one embodiment, the disc of ferromagnetic material is encapsulated in a pliable plastic material, and preferably a polymeric material, such as silicone rubber. This encapsulation may then continue directly and monolithically into the hinge.

Additionally or alternatively, the disc may be coated with silicone rubber, or a similar soft polymeric material, to enhance sealing to the valve seat in the closed position.

The at least one first retention element is preferably arranged to be positioned in a patient's bladder. The first retention element(s) may comprise at least one petal extending laterally outwards from the tubular body, and preferably at least two petals, and most preferably at least three petals. The petal(s) preferably extend essentially radially out from the tubular body. The petal configuration enables a very simple and efficient compression of the retention element(s) when the stent is to be inserted and removed, and at the same time unfolds into efficient anchors to ensure that the stent is maintained in place during use.

Preferably, the first retention element(s) has large extension in three directions, and a much smaller, or even non-existent extension in the fourth direction. Hereby, the retention elements conform to the normal interior shape of a female bladder, which makes use of the stent more comfortable. It also ensures that the stent does not rotate during use, but is maintained in a pre-definable position. This makes operation of the stent easier, since the valve is then maintained in a pre-determinable position. In one preferred embodiment, the at least one first retention element comprises three petals extending laterally outwards from the tubular body, preferably in a common plane, wherein two of the petals extend in essentially opposite directions, and one of the petals extend essentially perpendicular to the directions of the other petals.

In order to be even more compressible, and even smaller when compressed for removal and withdrawal, the petal(s) may further comprise central cut-out portions along the extension direction away from the tubular body. The cut-out may be totally within the petals, wherein each petal is formed as a loop around the opening. Alternatively, the cut out may be elongate and extend into a slit opening in the end being most remote from the tubular body. In this case, each petal comprises two arms, together embracing the cut-out central portion.

The at least one second retention element is preferably arranged to be positioned within the urethra of a patient, and at a position below the internal sphincter, and possibly also below the external sphincter. The second retention element(s) may form a flange extending radially outwards from the tubular body, and at least partly encircling the tubular body, and preferably being formed by two or more separate flange elements distributed around the circumference of the tubular body and with a separation distance between them. Provision of the flange as two or more separate parts makes the flanges easier to compress into a highly compressed state. The flange may, at least on a part thereof, have a conical shape, whereby the flange also has an extension in a length direction of the tubular body, and in a direction away from the first opening.

The second retention elements are preferably arranged at the second end of the tubular body, thereby enabling an even more compact compressed state for the stent.

However, the first and second retention elements may also be formed in other ways. For example, the first retention element(s) may be formed as a radially extending flange, and possibly also extending slightly upwards, away from the second end. Similarly, the second retention element(s) may be formed by petals, preferably having an extension both radially outwards from the tubular body, and downwards, in a direction away from the first end. The first and/or second retention element(s) may also, alternatively, comprise inflatable elements, such as annular inflatable elements arranged at, or in the vicinity of, the first and second ends, respectively.

At least a portion of the tubular body may further have a non-circular cross-section. This makes the stent more comfortable to use, since whereas the opening of the urethra is circular, the rest of it collapses into a flat or elliptic structure when there is no drainage of urine. However, as urine flows through, the whole urethra becomes circular. By making at least a part of the tubular body, such as the lower part and/or the central part, non-circular in cross-section, it better assumes the cross-sectional shape of the urethra, both in idle and active state. Further, the non-circular cross-sectional shape of the tubular body assists in preventing rotation of the stent during use, and maintains the stent in a pre-determinable rotational position.

The urethral stent preferably has a length which is less than the length of the urethra. The female urethra is typically 3-5 cm in length. The urethral stent preferably has a length less than 4 cm, and preferably less than 3 cm. Of the total length, it is preferred that the part intended to be in the bladder constitutes about ⅓ of the length, and the part intended to remain in the urethra is about ⅔ of the length. The radial extension of the first retention elements away from the tubular body, when unfolded, is preferably 10-25 mm in three directions, and most preferably about 15-20 mm, and 0-4 mm, and preferably 0-2 mm, in the fourth direction. The maximum width of the tubular body, when not compressed, is preferably in the range 5-9 mm, and preferably in the range 5-8 mm, and most preferably in the range 5-7 mm. The maximum extension of the stent in any cross-sectional direction perpendicular to the longitudinal direction and when the stent is compressed, is preferably equal to or less than 8 mm, and preferably equal to or less than 7 mm, and more preferably equal to or less than 6 mm, such as in the range of 5-7 mm. The disc of ferromagnetic material may e.g. have a diameter of 4-6 mm, and a thickness of 0.5-2 mm, and preferably about 1-1.5 mm.

The diameter of the first opening, of the lumen and the second opening are preferably at least 3 mm in diameter. It has been found that with an opening diameter of 3 mm, it takes around 40 s to empty a full bladder, which is considered fully acceptable.

The ferromagnetic material may form a permanent magnet, or may alternatively be a material attracted by such magnets, such as steel or iron.

According to another aspect of the disclosed embodiments, there is provided a bladder control assembly comprising a urethral stent in accordance with the previous discussion, and further comprising a source of magnetic attraction, said source of magnetic attraction being operable externally of the patient's body to bring the valve element to the open position.

In a preferred embodiment, the source of magnetic attraction is a permanent magnet, since it has been found that permanent magnet provides a magnetic field penetrating longer into human tissue than electromagnets of comparable size and weight. Thus, permanent magnets are easier and more convenient for the patient to carry around and handle in daily life.

In a particularly preferred embodiment, the source of magnetic attraction comprises a switchable permanent magnet device. Such a switchable permanent magnet device comprises two or more magnets which are rotatable in relation to each other, to provide a strong magnetic field in one rotational state, and a much weaker or even non-existent magnetic field in another rotational state. Such switchable permanent magnet devices are e.g. per se disclosed in U.S. Pat. Nos. 6,707,360 and 7,012,495, both said documents hereby being incorporated in their entirety by reference. Such switchable permanent magnet devices are also commercially available from e.g. Magswitch Technology, Denver, Colo. The use of such a switchable permanent magnet device for control of the valve element in the present urethral stent provides unexpected advantages. When activated, the switchable permanent magnet device provides a strong magnetic field, efficiently controlling the valve through the human tissue, and at the same time, when switched off, the magnet device is easy to carry around, e.g. in a handbag or in a pocket, and without any danger of accidental demagnetization of credit cards, or other disturbing influence on the environment.

The bladder assembly may further comprise an insertion aid, forming a cover to maintain the stent in a compressed state for insertion, and which enables release of the stent when at an appropriate position. The insertion aid may e.g. comprise a tubular compartment for accommodating the stent, and a wire or the like extending into the tubular compartment, useable to push out the stent at an appropriate position.

Upon use, the stent is inserted into the urethra, while in a compressed state, and is then release so that the first end is placed in the patent's bladder, and adapted to receive urine from the patient's bladder into the lumen, and the second end is placed within the urethra of the patient. When in place, the patient can at any time open the valve by means of the remote control, i.e. the external magnet, for draining of urine out through the stent.

These and other aspects of the disclosed embodiments will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein:

FIG. 2a illustrates the valve in a closed position, and FIG. 2b illustrates the valve in an open position;

FIGS. 7a-c illustrate various alternative embodiments of the first retention elements; and FIGS. 8a-c illustrate various alternative embodiments of the second retention elements.

DETAILED DESCRIPTION OF PREFERRED EMBODIMENTS

Figure 1:
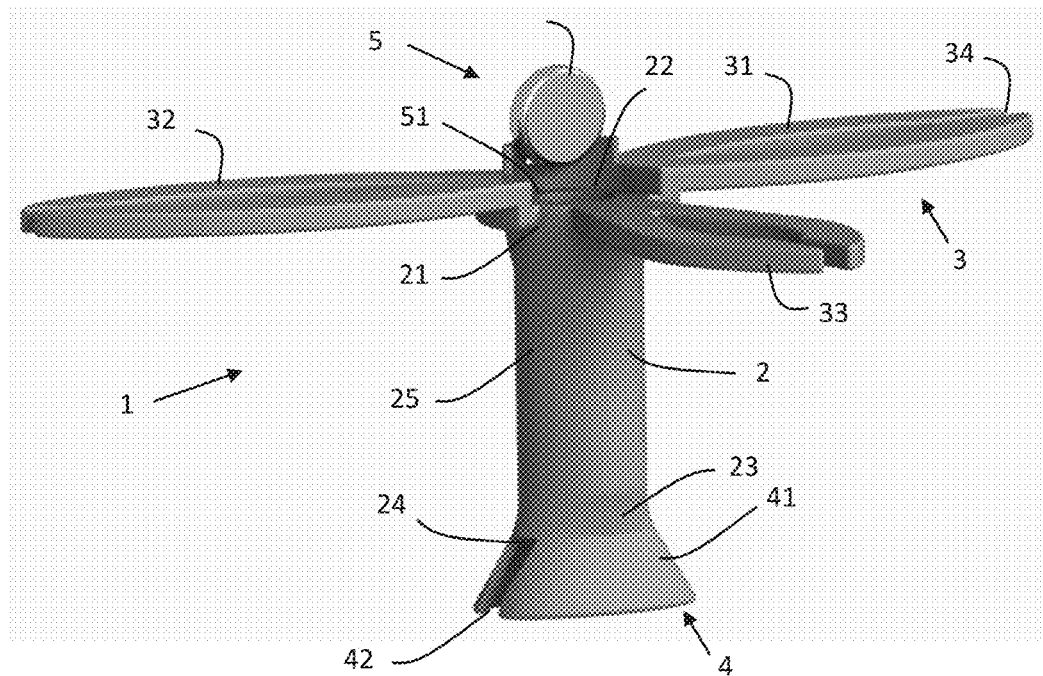
FIG. 1 is a perspective view from the side of a urethral stent in accordance with an embodiment.

In the following detailed description preferred embodiments of the invention will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations of the disclosed embodiments, e.g. the length of the medical device, etc. Further, even though the specific embodiments to be discussed in the following are related to a urethral stent specifically suited for female users, the same device, with slightly different dimensions, may also be used for males.

Referring to FIGS. 1-2, a urethral stent 1 comprises a tubular body 2 having a first end 21 with a first opening 22 and a second end 23 with a second opening 24, and a wall 25 defining a lumen extending between the two openings. The tubular body 2 here has a straight form, and with the same dimension over the entire length. However, alternative configurations, such as a slightly curved shape, a shape tapering upwards or downwards, etc., are also feasible. The tubular body may have a generally circular cross-section, but may also have a non-circular cross-section, such as a cross-section in the form of an oval, with rounded or pointed ends. The cross-sectional shape may also vary over the length of the tubular body, such as being circular at an upper part, including the first end 21, non-circular in a central part, and either circular or non-circular in a lower part, including the second end 23.

At least one first retention element 3 is connected to the tubular body at, or in the vicinity of, the first end. The first retention element(s) is arranged to be positioned in a patient's bladder. In the illustrative example, the retention elements are in the form of three petals 31, 32, 33. The petals extend radially outward from the tubular body, and preferably essentially in a common plane being perpendicular to the length direction of the tubular body 2. Two of the petals, 31 and 32, extend in essentially opposite direction, along a common line, whereas the third petal, 33, extends in a direction perpendicular to this common line. Hereby, the petals extend generally in three directions, but not in the fourth direction.

In the illustrative example, three petals are used. However, it is also feasible to use only one or two petals, or more than three petals.

The petals may be solid. However, preferably the petals are provided with cut-out openings, to reduce the amount of material and make the petals more compressible. In the illustrative example, the cut-out portions 34 are provided as elongate, central cut-outs, extending from a starting position at a short distance from the tubular body, and extending all the way to the remote ends of the petals. The cut-outs are here wider in the middle part of the petal, and narrower at the ends, towards the tubular body and towards the remote end of the petals. Thus, each petal here comprises two arms, which are curved to embrace the central elongate opening, and which meets at a relatively narrow gap at the remote end. However, other forms of cut-outs may also be used. For example, the arms may be connected also at the remote ends, thereby encircling a central cut-out, or one or several elongate slit openings may be formed, instead of the enlarged opening shown in the illustrative example.

The stent further comprises at least one second retention element 4, connected to the tubular body 2 at a distance from the first end 21 and the first retention element(s) 3. The second retention element(s) is arranged to be positioned within the urethra of a patient. Here, the second retention element forms a flange 41 extending radially outwards from the tubular body 2, and at least partly encircling the tubular body. In the illustrative example, the flange is provided by two separate flange elements distributed around the circumference of the tubular body and with a separation 42 between them. However, a single, continuous flange may also be used, as well as more than two separate flange elements.

The flange, or at least on a part thereof, has a conical shape, whereby the flange has an extension both radially outwards, and downwards in a length direction of the tubular body, and in a direction away from the first opening.

Figures 2A, 2B:
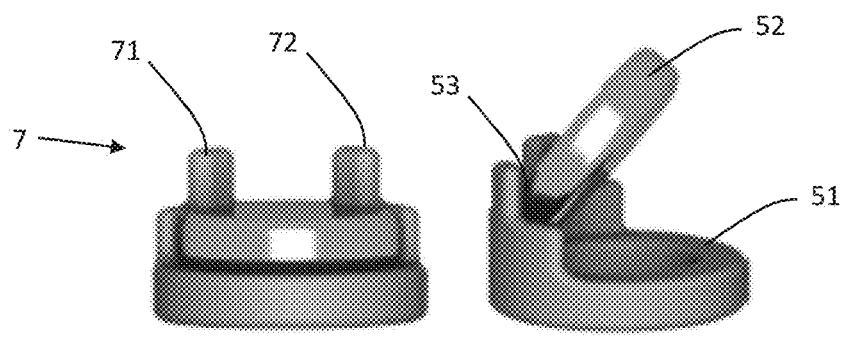
FIGS. 2a and 2b are detailed view of the valve in the urethral stent of FIG. 1, where

At the first end 21, there is further provided a valve 5. The valve comprises a valve seat 51 formed by the first opening 22 and a valve element 52 being pivotably connected to the tubular body and/or the valve seat by a hinge 53 connected to the tubular body 2 at one side of the first opening 22. Hereby, the valve element is pivotable between a closed position, as shown in FIG. 2a, in which the valve element 52 is in engagement with the valve seat 51, thereby closing the lumen within the tubular body, and an open position, as shown in FIG. 2b, in which the valve element 52 is pivoted away from the valve seat 51, thereby opening the lumen.

The valve element is at least partly made of a ferromagnetic material and has an area which exceeds the area of the lumen opening. The ferromagnetic material is preferably provided in the form of a disc of ferromagnetic material. The disc may be connected to the hinge, e.g. by adhesive, or be integrally formed with the hinge, e.g. by being encapsulated in a pliable plastic material, and preferably a polymeric material, such as silicone rubber, which monolithically continues into the hinge.

The stent further comprises at least one pivot restriction element 7 arranged in the vicinity of the first opening 22 and in the vicinity of the hinge 53, and protruding away from tubular body 2. In the illustrative example, the pivot restriction element comprises at least one finger extending essentially in the length direction of the tubular body. In the illustrative example, two fingers 71, 72 are provided, on each side of the hinge.

All parts of the urethral stent, apart from the ferromagnetic material, can be made by plastic material(s), and preferably relatively elastic material, such as a polymer or a polymer blend. For example, the parts may be made in silicone rubber, polyurethane(s) or thermoplastic elastomer(s). The various parts may be made of the same or different material. The parts may also be formed in a single process, to be monolithically integrated with each other, such as by molding, injection molding, 3D printing or the like.

Figure 3:
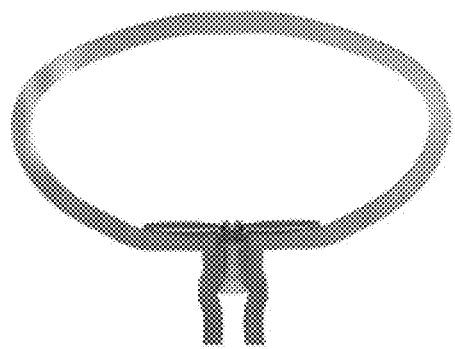
FIG. 3 is a schematic illustration of the urethral stent of FIG. 1 when inserted into the bladder and urethra.

In FIG. 3, the above-discussed urethral stent is arranged within a schematically illustrated urethra of a patient. In this position, the first retention elements are arranged within the bladder, preventing movement of the stent downwards, towards the urethra orifice, and the second retention elements are arranged within the urethra, and below the sphincter, thereby preventing further movement upwards, into the bladder. As clearly seen in FIG. 3, the length and dimensions of the stent are such that the stent is fully contained within the urethra and bladder, and does not extend into the lower parts of the urethra, or out through the urethra orifice.

Figure 4:
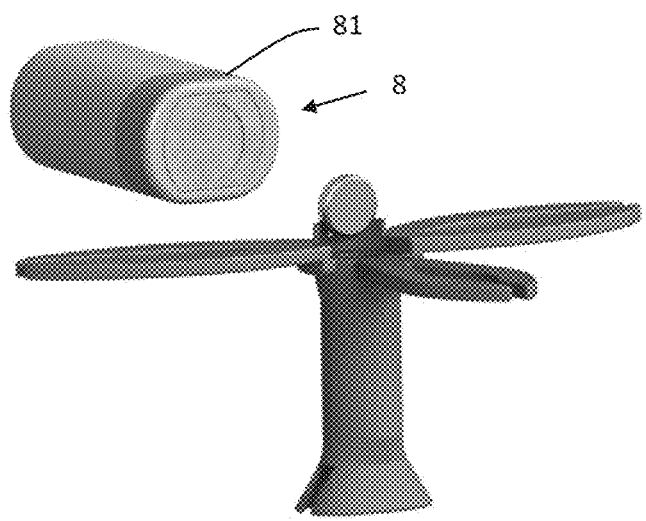
FIG. 4 is a perspective view from the side illustrating of a bladder control assembly in accordance with an embodiment.

Referring to FIG. 4, a bladder control assembly comprises a urethral stent as discussed above, and a source of magnetic attraction. The source 8 of magnetic attraction is operable externally of the patient's body to bring the valve element to the open position.

Figure 5:
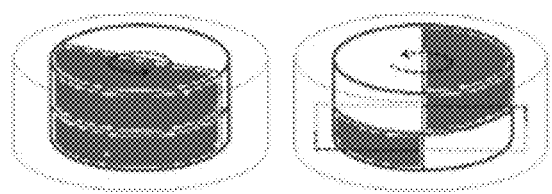
FIG. 5 is a schematic illustration of the switchable permanent magnet device of the assembly in FIG. 4.

In an illustrative embodiment, the source of magnetic attraction comprises a switchable permanent magnet device 81. Such a device is illustrated schematically in FIG. 5. The device comprises two permanent magnets that are rotational in relation to each other, so that in a first rotation al position, illustrated in the left hand side of FIG. 5, a strong magnetic field is provided, whereas in a second rotational position, illustrated in the right hand side of FIG. 5, a weak or non-existent magnetic field is provided. Such switchable permanent magnet devices are per se known from e.g. U.S. Pat. Nos. 6,707,360 and 7,012,495, both said document hereby being incorporated in their entirety by reference.

Figure 6:
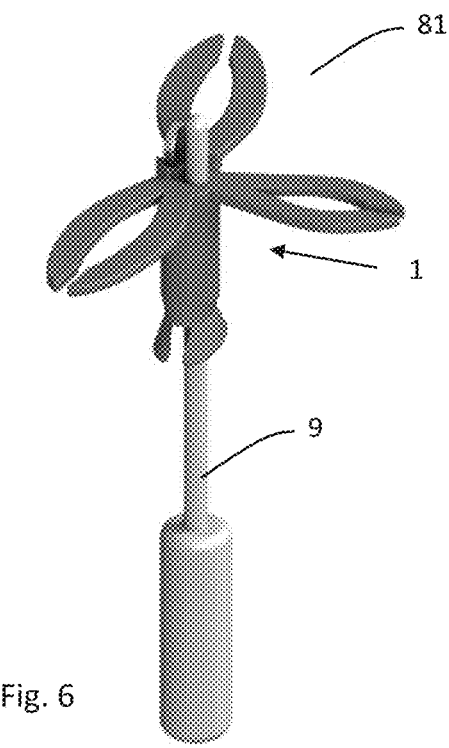
FIG. 6 is a schematic illustration of emergency opening of the urethral stent of FIG. 1.

For the unlikely event of a malfunction, where the valve cannot be opened by the external magnet, or when the external magnet is not at hand, it is also possible to mechanically force the valve to an open state. This is illustrated in FIG. 6. To this end, a catheter 9, or a stent or the like, may be inserted into the urethra, and into the tubular body, so that the valve element is pivoted upwards.

Specific embodiments of the invention have now been described. However, several alternatives are possible, as would be apparent for someone skilled in the art. For example, other types of retention elements may be used. Some further examples of such alternative retention elements are illustrated in FIGS. 7a-c and 8a-c.

FIGS. 7a-c schematically illustrate some alternatives for use as first retention elements. In FIG. 7a, the retention elements are formed as solid petals, and here also arranged to be partly overlapping each other. In the embodiment of FIG. 7b, the retention element is formed as an annular, inflatable member. In FIG. 7c, the retention element is a single petal, extending over essentially a half circle around the tubular body.

FIGS. 8a-c schematically illustrate some alternatives for use as second retention elements. In FIG. 8a, the retention element is formed as a solid, continuous flange, extending around the tubular body. In the embodiment of FIG. 8b, the retention element is also a continuous flange, but here having an undulated lower end. In the embodiment of FIG. 8c, the retention element is formed as an annular, inflatable member.

Such and other obvious modifications must be considered to be within the scope of the disclosed embodiments. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

The invention claimed is:

1. A urethral stent for arrangement in the urethra of a patient, comprising:
   a tubular body having a first end with a first opening and a second end with a second opening, and a wall defining a lumen extending therethrough between the first and second openings;
   at least one first retention element connected to the tubular body at, or in the vicinity of, the first end;
   at least one second retention element, connected to the tubular body at a distance from the first end and the first retention element;
   a valve arranged at the first end, the valve comprising a valve seat formed by the first opening and a valve element being pivotably connected to the tubular body and/or the valve seat by a hinge connected to the tubular body and/or the valve seat at one side of the first opening, whereby the valve element is pivotable between a closed position, in which the valve element is in engagement with the valve seat at the first opening, thereby closing the lumen, and an open position in which the valve element is pivoted away from the valve seat, thereby opening the lumen, wherein the valve element is at least partly made of a ferromagnetic material and has an area which exceeds the area of the first opening; and at least one pivot restriction element arranged in the vicinity of the first opening and in the vicinity of the hinge, and protruding away from tubular body.

2. The urethral stent of claim 1, wherein the pivot restriction element comprises at least one finger extending essentially in the length direction of the tubular body.

3. The urethral stent of claim 1, wherein the valve element comprises a disc of ferromagnetic material.

4. The urethral stent of claim 3, wherein the disc is encapsulated in a pliable plastic material.

5. The urethral stent of claim 3, wherein the disc is encapsulated in a pliable polymeric material.

6. The urethral stent of claim 1, wherein the at least one first retention element is arranged to be positioned in a patient's bladder.

7. The urethral stent of claim 1, wherein the at least one first retention element comprises at least one petal extending laterally outwards from the tubular body.

8. The urethral stent of claim 1, wherein the at least one first retention element comprises at least two petals.

9. The urethral stent of claim 1, wherein the at least one first retention element comprises at least three petals.

10. The urethral stent of claim 1, wherein the at least one first retention element comprises three petals extending laterally outwards from the tubular body, wherein two of the petals extend in essentially opposite directions, and one of the petals extend essentially perpendicular to the directions of the other petals.

11. The urethral stent of claim 10, wherein the three petals extends in a common plane.

12. The urethral stent of claim 7, wherein the petal(s) comprise central cut-out portions along the extension direction away from the tubular body.

13. The urethral stent of claim 1, wherein the at least one second retention element is arranged to be positioned within the urethra of a patient.

14. The urethral stent of claim 1, wherein the at least one second retention element forms a flange extending radially outwards from the tubular body, and at least partly encircling the tubular body.

15. The urethral stent of claim 14, wherein the flange is formed by two or more separate flange elements distributed around the circumference of the tubular body and with a separation distance between them.

16. The urethral stent of claim 14, wherein the flange, at least on a part thereof, has conical shape, whereby the flange also has an extension in a length direction of the tubular body, and in a direction away from the first opening.

17. The urethral stent of claim 1, wherein at least a portion of the tubular body has a non-circular cross-section.

18. The urethral stent of claim 1, wherein a length of the stent is less than the length of the urethra.

19. A bladder control assembly comprising a urethral stent in accordance with claim 1, and further comprising a source of magnetic attraction, said source of magnetic attraction being operable externally of the patient's body to bring the valve element to the open position.

20. The bladder control assembly of claim 19, wherein the source of magnetic attraction comprises a switchable permanent magnet device.

* * * * *